United States Patent
Pridgen

(10) Patent No.: US 11,583,495 B2
(45) Date of Patent: *Feb. 21, 2023

(54) NASAL COMPOSITION COMPRISING A MUCOADHESIVE POLYMER

(71) Applicant: Northriver Pharm, LLC, Tuscaloosa, AL (US)

(72) Inventor: William L. Pridgen, Tuscaloosa, AL (US)

(73) Assignee: Northriver Pharm, LLC, Tuscaloosa, AL (US)

( * ) Notice: Subject to any disclaimer, the term of this patent is extended or adjusted under 35 U.S.C. 154(b) by 272 days.

This patent is subject to a terminal disclaimer.

(21) Appl. No.: 17/022,694

(22) Filed: Sep. 16, 2020

(65) Prior Publication Data

US 2021/0000737 A1 Jan. 7, 2021

Related U.S. Application Data

(63) Continuation of application No. 16/037,243, filed on Jul. 17, 2018, now Pat. No. 10,786,449.

(60) Provisional application No. 62/533,351, filed on Jul. 17, 2017.

(51) Int. Cl.

| | | |
|---|---|---|
| A61K 9/00 | (2006.01) |
| A61K 31/573 | (2006.01) |
| A61K 31/05 | (2006.01) |
| A61K 45/06 | (2006.01) |
| A61K 47/46 | (2006.01) |
| A61P 21/00 | (2006.01) |
| A61K 47/34 | (2017.01) |
| A61K 31/52 | (2006.01) |
| A61K 31/522 | (2006.01) |
| A61P 3/10 | (2006.01) |
| A61P 31/12 | (2006.01) |
| A61K 47/38 | (2006.01) |
| A61K 47/32 | (2006.01) |
| A61K 47/10 | (2017.01) |
| A61K 31/43 | (2006.01) |
| A61K 47/36 | (2006.01) |
| A61K 31/245 | (2006.01) |
| A61K 38/28 | (2006.01) |

(52) U.S. Cl.
CPC ............. *A61K 9/006* (2013.01); *A61K 31/05* (2013.01); *A61K 31/245* (2013.01); *A61K 31/43* (2013.01); *A61K 31/52* (2013.01); *A61K 31/522* (2013.01); *A61K 31/573* (2013.01); *A61K 38/28* (2013.01); *A61K 45/06* (2013.01); *A61K 47/10* (2013.01); *A61K 47/32* (2013.01); *A61K 47/34* (2013.01); *A61K 47/36* (2013.01); *A61K 47/38* (2013.01); *A61K 47/46* (2013.01); *A61P 3/10* (2018.01); *A61P 21/00* (2018.01); *A61P 31/12* (2018.01)

(58) Field of Classification Search
CPC ...... A61K 31/05; A61K 31/573; A61K 45/06; A61K 2300/00
See application file for complete search history.

(56) References Cited

U.S. PATENT DOCUMENTS

| | | |
|---|---|---|
| 3,457,348 A | 7/1969 | Nash et al. |
| 5,762,963 A | 6/1998 | Byas-Smith |
| 5,906,811 A | 5/1999 | Hersh |
| 6,159,473 A | 12/2000 | Watkins et al. |
| 6,372,258 B1 | 4/2002 | Platz et al. |
| 6,391,330 B1 | 5/2002 | Ross |
| 8,157,767 B2 | 4/2012 | Rozenberg et al. |
| 2003/0077304 A1 | 4/2003 | McCadden |
| 2009/0123570 A1 | 5/2009 | Warner et al. |
| 2017/0049789 A1 | 2/2017 | Bhalani et al. |

FOREIGN PATENT DOCUMENTS

| | | |
|---|---|---|
| WO | WO-1997/038662 A2 | 10/1997 |
| WO | WO-1998/046245 A1 | 10/1998 |
| WO | WO-2002/058610 A1 | 8/2002 |
| WO | WO-2003/059390 A1 | 7/2003 |
| WO | WO-2008/075102 A1 | 6/2008 |

OTHER PUBLICATIONS

Ho, C., et al.; "Approach to Sore Throat", Peds Cases, Pediatrics for Medical Students, Apr. 16, 2016, pp. 1-8.
International Search Report (ISR) from corresponding PCT Application No. PCT/US2018/042385, dated Sep. 17, 2018.
Office Action (Non-final) dated Sep. 13, 2019 issued in U.S. Appl. No. 16/037,243.
Office Action (Final) dated Jun. 15, 2020 issued in U.S. Appl. No. 16/037,243.

*Primary Examiner* — Barbara P Badio
(74) *Attorney, Agent, or Firm* — Harness, Dickey & Pierce, P.L.C.

(57) ABSTRACT

The present disclosure relates to a method for delivering a mucoadhesive composition to the oral cavity of a subject. The mucoadhesive composition comprises one or more active agents, a mucoadhesive polymer, and water. The present disclosure is further related to a method for treating a disease, disorder, or condition, such as pharyngitis, aphthous stomatitis (canker sore), bacterial infection, radiation-induced mucositis, fibromyalgia, and diabetes, comprising administering the mucoadhesive composition to the oral cavity of a subject. The present disclosure is also related a mucoadhesive composition comprising one or more active agents, a mucoadhesive polymer, and water.

14 Claims, 7 Drawing Sheets

NASAL COMPOSITION COMPRISING A MUCOADHESIVE POLYMER

CROSS-REFERENCE TO RELATED APPLICATION

This application is a continuation application of U.S. application Ser. No. 16/037,243, filed 17 Jul. 2018, which claims the benefit and priority to U.S. Provisional Application No. 62/533,351, filed on 17 Jul. 2017. The entire disclosures of the applications identified in this paragraph are incorporated herein by references.

FIELD

The present disclosure relates to mucoadhesive compositions, spray devices comprising the composition, methods for delivering the composition, and methods for treating a disease using the composition.

BACKGROUND

Oral, transmucosal delivery represents an attractive route of administration for pharmaceutical agents. It combines the ease of per oral administration while avoiding hepatic first-pass metabolism and enzymatic degradation of the agent within the gastrointestinal tract. Furthermore, the mucosa of the oral cavity is relatively permeable with a rich blood supply, displays quick stress-recovery times, and lacks Langerhans cells, rendering it resistant to potential allergic reactions. Transmucosal oral delivery allows for both systemic and local delivery of a pharmaceutical agent, which makes this administration route extremely versatile with respect to the active agents to be delivered. Also advantageously, transmucosal oral delivery is highly acceptable by patients.

Mucoadhesion occurs when a composition adheres to the mucosal layer. Polymers within a composition may adhere to the mucosal layer through any number of different mechanisms, including electrostatic attraction, hydrogen bonding, and polymer diffusion into the mucosal layer. A mucoadhesive composition may comprise a polymer in a carrier, which aids in the mucoadhesion, as well as a pharmaceutically active agent, which accompanies the polymer and carrier to a mucosal surface. The pharmaceutical agent adheres to the mucosa and may either exert a local effect or enter the circulatory system to induce a systemic effect.

Transmucosal oral delivery allows for direct application of a therapeutic agent to the oral cavity for local or systemic effect. For example, buccal administration of insulin can be effective to treat diabetes (Heinemann, et al., *J. Diabetes Sci. Technol.*, 2009). Penicillin can be systemically administered when applied to the sublingual surface (Dolkart, et al., *Q. Bull. Northwest. Univ. Med. Sch.* 1946). Bioadhesive buccal tablets of triamcinolone acetonide are also known (see, for example, Mumtaz, et al., *Int. J. Pharm.* 1995). Transmucosal oral spray formulations must fit specific criteria to be therapeutically useful. They need to be thin enough to be effectively sprayed to a target area yet thick enough to adhere intact to the oral mucosa. Further, they should be relatively insoluble to saliva and withstand repeated swallows to allow the active agent(s) to be absorbed. Finally, they should be sufficiently soothing, be not unpleasant in either taste or feeling, and composed of nontoxic components.

Acute pharyngitis is inflammation of the pharynx (back of the throat) and the most common cause of a sore throat. Viral pharyngitis accounts for 40%-80% of all adult cases, with 5%-15% being of bacterial origin. Patients suffering acute pharyngitis may have trouble swallowing and/or breathing, a cough, a fever, or a combination of symptoms. Analgesics, antipyretics, and topical anesthetics represent the current standard of care for symptomatic relief of pharyngitis. These strategies include anesthetic gargles and lozenges (e.g., benzocaine), neither of which are efficient for delivery to the posterior oropharynx. Current treatment of the anterior pharyngeal region, such as for treating aphthous stomatitis (canker sores), includes direct application to the ulcer with a dental steroid paste (e.g., Kenalog in orabase). This composition resists washout and remains long enough to deliver a therapeutically effective amount of the drug. However, dental pastes are not convenient to treat pharyngitis because they are difficult to apply to the posterior oropharynx. Therefore, a therapeutic regimen is needed for delivery of a pharmaceutical agent to the posterior oropharynx to treat pharyngitis. Currently, there is no oral spray with sufficient viscosity to adhere to the posterior mucosa of the posterior oropharynx, yet thin enough for coverage of the affected area.

WO 1998/046245 describes a composition containing phospholipid for delivery via spray to the posterior pharyngeal region to treat sleep apnea by lowering mucosal surface tension.

U.S. Pat. No. 5,762,963 describes topical application of a capsaicinoid to impart pharyngeal analgesia.

U.S. Pat. No. 6,391,330 describes nasal and pharyngeal sprays comprising proanthocyanidins and ascorbic acid in a saline solution to protect nasal and oral mucosa from noxious viruses, bacteria, fungi, and excessive drying.

U.S. Pat. No. 5,906,811 describes intra-oral antioxidant preparations comprising glutathione, ascorbic acid, selenium, and a sulfur-containing amino acid.

WO 2002/058610 describes spray formulations comprising tyloxapol or related alkylaryl polyether alcohol polymers.

U.S. Pat. No. 6,159,473 describes a spray for sore throats comprising *Piper methysticum* (Kava Kava) as a replacement for phenol and additional herbs.

U.S. Pat. No. 6,372,258 describes a dispersible dry powder comprising a drug and a hydrophobic amino acid and methods of making said powder. The dry powder can be delivered to the throat via a dry powder inhaler.

US Patent Publication No. 2009/0123570 describes compositions comprising hypertonic saline for treating a sore throat.

WO 1997/038662 describes buccal aerosol sprays comprising a polar solvent, an active agent, and a flavoring.

WO 08/075102 describes transmucosal delivery of active agents, particularly agents that affect the central nervous system, that are within submicron particles.

U.S. Pat. No. 8,157,767 describes devices for cooling the nasal cavity

ANDOSEPT® is an oral spray comprising chlorohexidine gluconate and benzydamine HCl that is useful for treating viral pharyngitis.

SUMMARY

In one embodiment, there is provided a method for delivering an active agent to the oral cavity, the method comprising administering a mucoadhesive composition to the oral cavity of a subject, wherein said mucoadhesive composition comprises a therapeutically effective amount of one or more active agents, a mucoadhesive polymer, and water. In various embodiments, the mucoadhesive polymer is selected from the group consisting of sodium alginate, chitosan, guar gum, xanthan gum, pectin, hydroxyethyl cellulose (HEC), hydroxypropyl cellulose (HPC), hydroxypropylmethyl cellulose (HPMC), sodium carboxymethyl cellulose, poly(ethylene oxide), poly(acrylic acid), poloxamer, galactomannan, glucomannan, carrageenan, hyaluronic acid, gelatin, lectin, fimbrial proteins, and combinations thereof. In some embodiments, a viscosity of the mucoadhesive polymer is between about 50 and about 600 mPa·s.

In another embodiment, there is provided a method for treating a disease, disorder, or condition comprising administering a mucoadhesive composition to the oral cavity of a subject in need thereof. In various embodiments, the method is used for treating a disease, disorder, or condition selected from the group consisting of pharyngitis, aphthous stomatitis (canker sore), bacterial infection, radiation mucositis, fibromyalgia, chronic fatigue syndrome (CFS), myalgic encephalomyelitis/chronic fatigue syndrome (ME/CFS), and diabetes.

In another embodiment, there is provided a mucoadhesive composition comprising one or more active agents, a mucoadhesive polymer, and water. In various embodiments, the mucoadhesive polymer is selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer, galactomannan, glucomannan, carrageenan, hyaluronic acid, gelatin, lectin, fimbrial proteins, and combinations thereof. In some embodiments, a viscosity of the mucoadhesive polymer is between about 50 and about 600 mPa·s.

In yet another embodiment, there is provided a spray device comprising a mucoadhesive composition described herein.

Further areas of applicability will become apparent from the description provided herein. The description and specific examples in this summary are intended for purposes of illustration only, and are not intended to limit the scope of the present disclosure.

DETAILED DESCRIPTION

Figure 1A:
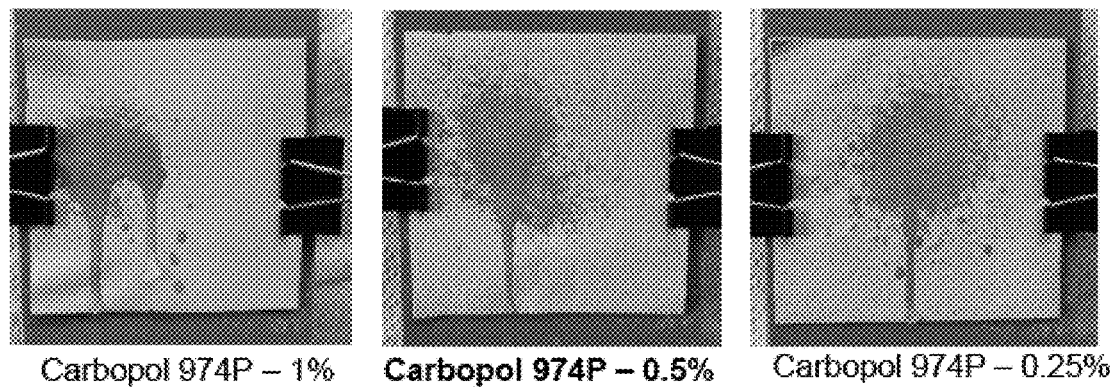
FIGS. 1A, 1B, 1C, 1D, 1E, and 1F compare the spray properties of various mucoadhesive compositions comprising a mucoadhesive polymer and water, as follows: 1A: CARBOPOL® 974P; 1B: CARBOPOL® 971P; 1C: CARBOPOL® EDT 2020 NF; 1D: CARBOPOL® 934P; 1E: Pectin; and 1F: Chitosan.
Figure 1B:
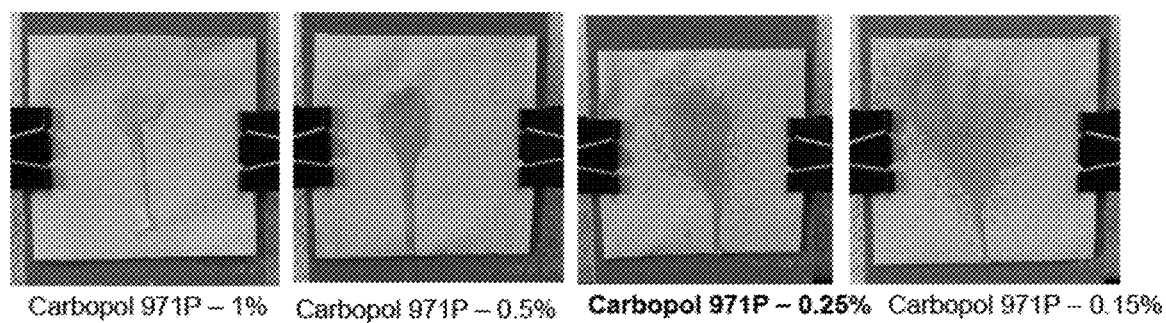
Figure 1C:
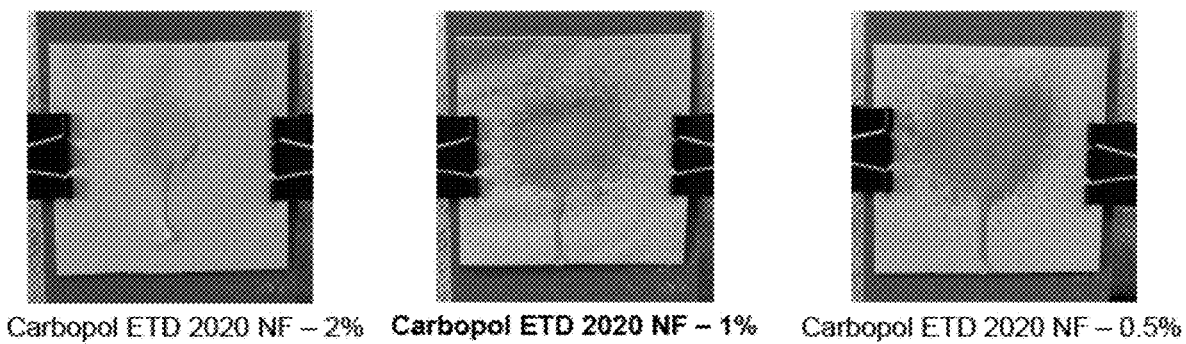
Figure 1D:
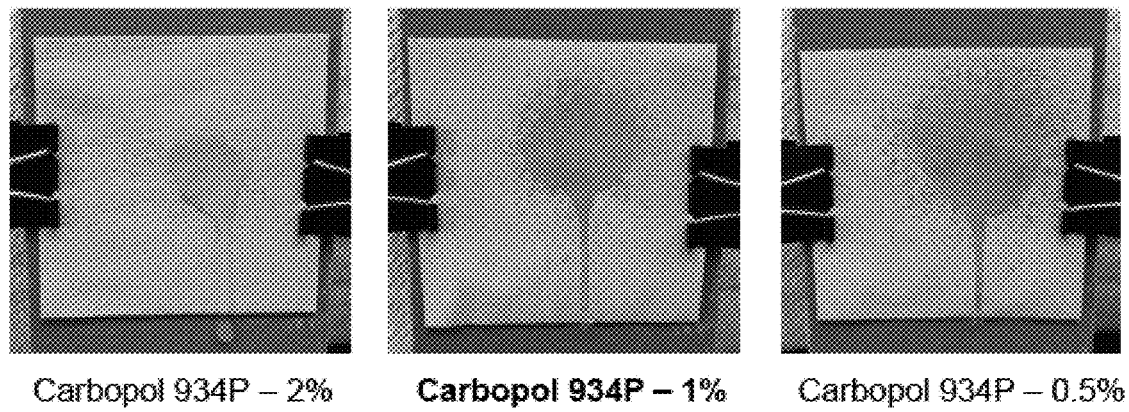
Figure 1E:
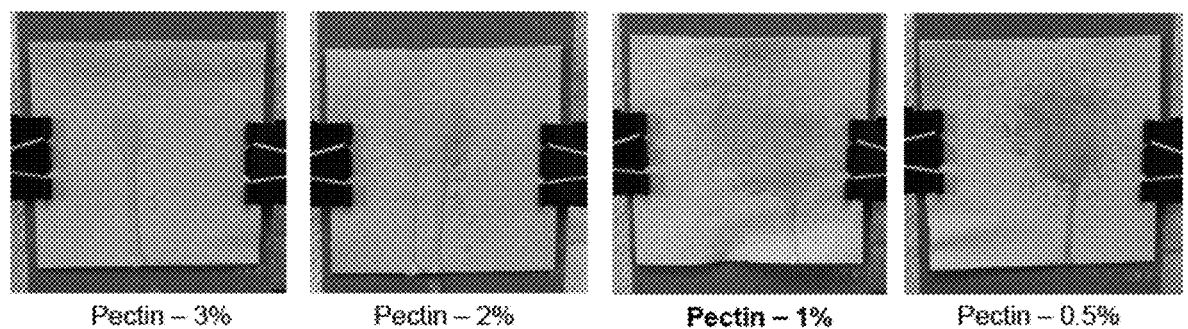
Figure 1F:
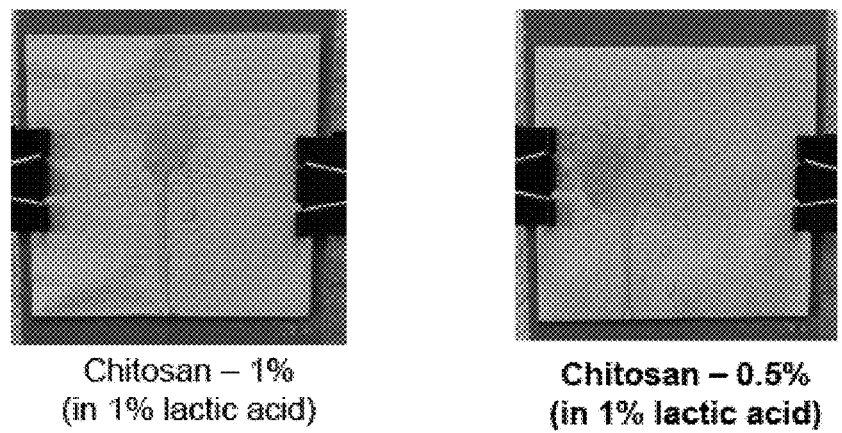

The following description is merely exemplary in nature and is not intended to limit the present disclosure, application, or uses.

A. Definitions

The term "active agent" means a compound, or combination of compounds, with medicinal and/or therapeutic properties, which are suitable for use in pharmaceutical preparations, generally considered as safe for such use, officially approved by a regulatory agency of a national or state government for such use, or being listed in the U.S. Pharmacopoeia, or other generally recognized pharmacopoeia for use in animals, and more particularly, humans. "Active agents" include, but are not limited to, steroids, anti-viral agents, antibiotics, anesthetics, analgesics, hormones, opioids, and combinations thereof. Specific active agents include, but are not limited to, triamcinolone, acyclovir, famcyclovir, valacyclovir, benzocaine, phenol, penicillin, amoxicillin, insulin, naltrexone, dextro-naltrexone, and combinations thereof.

The term "therapeutically effective amount" refers to an amount of an active agent that, when administered to a subject for treating a disease, is sufficient to effect treatment for the disease. "Therapeutically effective amount" can vary depending on the compound; the disease and its severity; and the age, weight, etc. of the subject to be treated.

The term "mucoadhesive composition" refers to a composition that adheres to the mucosa or mucosal surface. The mucoadhesion can occur by any mechanism, including, but not limited to, electrostatic attraction, hydrogen bonding, low surface tension, and polymer diffusion into the mucosal layer. The term "mucosa" or "mucosal surface" refers to any surface or anatomical location over which mucus is produced. "Mucosa" and "mucosal surface" include, but are not limited to, the oral, nasal, ocular, aural, vaginal, anal, gastric, and intestinal cavities.

The term "mucoadhesive polymer" refers to compounds that adhere to the mucosa or mucosal surface. Mucoadhesive polymers include all classes of mucoadhesive polymers, including anionic polymers (e.g., alginate, xanthan gum, carageenan), cationic polymers (e.g., chitosan), non-ionic polymers (e.g., guar gum, galactomannan, gluconamman, amphoteric polymers, polymeric thiomers, polymers with acrylate end groups, dendrimers, boronic acid copolymers, synthetic glycopolymers, and polymeric blends and complexes.

The term "treat" (and corresponding terms "treatment" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents or delays the occurrence of a condition in a subject. The term "restorative treatment" refers to treatment that halts the progression of, reduces the pathologic manifestations of, or entirely eliminates a condition in a subject.

The term "spray device" refers to any device which is capable of ejecting a volume of a mucoadhesive composition in the form of a spray. It may include an operating mechanism (e.g., spray head or pump) attached to a fluid reservoir. The spray device may be manual or pressurized.

B. Pharmaceutical Compositions

The present disclosure describes mucoadhesive compositions comprising an active agent, a mucoadhesive polymer, and water.

In one embodiment is provided a mucoadhesive composition comprising a therapeutically effective amount of an active agent, which encompasses both a single pharmaceutical compound and a combination of pharmaceutical compounds, a mucoadhesive polymer, and water. The mucoadhesive polymer may be selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer, galactomannan, glucomannan, carrageenan, hyaluronic acid, gelatin, lectin, fimbrial proteins, and combinations thereof. Particular poly(acrylic acid) polymers include polymers within the CARBOPOL®® polymer family. These polymers are all high molecular weight, crosslinked polyacrylic acid polymers, differing by crosslink density. In a particular embodiment, the mucoadhesive polymer is selected from the group consisting of CARBOPOL®® 974P (USP/NF: Carbomer Homopolymer Type B), CARBOPOL®® 971P (USP/NF: Carbomer Homopolymer Type A), CARBOPOL®® ETD 2020 NF (USP/NF: Carbomer Interpolymer Type B), CARBOPOL®® 934P (USP/NF: Carbomer 934P), pectin, chitosan, and combinations thereof. In some embodiments, a viscosity of the mucoadhesive polymer is between about 50 and about 600 mPa·s.

In another embodiment, the mucoadhesive polymer is present in an amount of about 0.01 to about 30%, by weight of the composition. In another embodiment, the mucoadhesive polymer is present in the amount of about 0.15 to about 15%, by weight of the composition. In another embodiment, the mucoadhesive polymer is present in an amount of about 0.25 to about 3.0%, by weight, of the composition. In a particular embodiment, the mucoadhesive polymer is present in an amount of about 0.25%, about 0.5%, about 1.0%, about 2.0%, about 3.0%, about 4%, about 6%, about 10%, or about 15% by weight, of the composition.

In an embodiment, the polymer is CARBOPOL® 974P in an amount of between about 0.25 and about 1%, by weight, of the composition, for example at about 0.25 wt %, about 0.5 wt %, or about 1 wt %. In an embodiment, the polymer is CARBOPOL® 971P in an amount of between about 0.15 and about 1%, by weight, of the composition, for example at about 0.15 wt %, about 0.25 wt %, about 0.5 wt %, or about 1 wt %. In an embodiment, the polymer is CARBOPOL® 934P in an amount of between about 0.5 and about 2%, by weight, of the composition, for example at about 0.5 wt %, about 1 wt %, or about 2 wt %. In an embodiment, the polymer is pectin in an amount of between about 0.5 and about 3%, by weight, of the composition, for example at about 0.5 wt %, about 1 wt %, about 2 wt %, or about 3 wt %. In an embodiment, the polymer is chitosan in an amount of between about 0.5 and about 1%, by weight, of the composition, for example at about 0.5 wt % or about 1 wt %. In an embodiment, the polymer is sodium carboxymethylcellulose (90 k g/mol) in an amount of between about 1 and about 4%, by weight, of the composition, for example at about 1 wt %, about 2 wt % or about 4 wt %. In an embodiment, the polymer is sodium carboxymethylcellulose (250 k g/mol) in an amount of between about 0.5 and about 2%, by weight, of the composition, for example at about 0.5 wt %, about 1 wt % or about 2 wt %. In an embodiment, the polymer is hydroxyethylcellulose (90 k g/mol) in an amount of between about 2 and about 6%, by weight, of the composition, for example at about 2 wt %, about 3 wt % or about 6 wt %. In an embodiment, the polymer is hydroxyethylcellulose (250 k g/mol) in an amount of between about 1 and about 2%, by weight, of the composition, for example at about 1 wt %, or about 2 wt %. In an embodiment, the polymer is hydroxypropylmethylcellulose (80-120 cP) in an amount of between about 0.5 and about 2%, by weight, of the composition, for example at about 0.5 wt %, about 1 wt % or about 2 wt %. In an embodiment, the polymer is hydroxypropylmethylcellulose (2600-5600 cP) in an amount of between about 0.25 and about 1%, by weight, of the composition, for example at about 0.25 wt %, about 0.5 wt % or about 1 wt %. In an embodiment, the polymer is hydroxypropylcellulose (80 k g/mol) in an amount of between about 1 and about 4%, by weight, of the composition, for example at about 1 wt %, about 2 wt % or about 4 wt %. In an embodiment, the polymer is hydroxypropylcellulose (100 k g/mol) in an amount of between about 1 and about 4%, by weight, of the composition, for example at about 1 wt %, about 2 wt % or about 4 wt %. In an embodiment, the polymer is polyethylene oxide (300 k g/mol) in an amount of between about 0.5 and about 3%, by weight, of the composition, for example at about 0.5 wt %, about 1 wt %, or about 3 wt %. In an embodiment, the polymer is Pluronic F-127 in an amount of between about 10 and about 15%, by weight, of the composition, for example at about 10 wt %, or about 15 wt %. In an embodiment, the polymer is sodium alginate in an amount of between about 0.5 and about 2%, by weight, of the composition, for example at about 0.5 wt %, about 1 wt %, or about 2 wt %. In an embodiment, the polymer is xanthan gum in an amount of between about 0.25 and about 1%, by weight, of the composition, for example at about 0.25 wt %, about 0.5 wt %, or about 1 wt %.

In another embodiment, the active agent is selected from the group consisting of steroids, anti-viral agents, antibiotics, anesthetics, analgesics, hormones, opioids, and combinations thereof. In a further embodiment, the active agent is selected from the group consisting of triamcinolone, acyclovir, famcyclovir, valacyclovir, benzocaine, phenol, penicillin, amoxicillin, insulin, naltrexone, dextro-naltrexone, and combinations thereof.

In another embodiment, the pharmaceutical composition further comprises an additional anesthetic. In a further embodiment, the additional anesthetic is selected from the group consisting of benzocaine, phenol, or combinations thereof.

In another embodiment, the active agent comprises triamcinolone.

In another embodiment, the active agent comprises the combination of triamcinolone and either benzocaine or phenol.

In a particular embodiment, the active agent is the combination of triamcinolone, acyclovir, and either benzocaine or phenol.

In another embodiment, the active agent comprises famcyclovir or valacyclovir.

In another embodiment, the active agent comprises a penicillin.

In another embodiment, the active agent comprises an insulin.

In a particular embodiment, the active agent comprises triamcinolone and either benzocaine or phenol and the mucoadhesive polymer is CARBOPOL® ETD 2020 NF, CARBOPOL® 934P, CARBOPOL® 971P, or CARBOPOL® 974P NF.

In another embodiment, the composition further comprises a preservative. In some embodiments, the preservative is a paraben. In some embodiments, the preservative may be present in an amount of about 0.00001% to about 0.01%, by weight, of the composition.

In another embodiment, the composition further comprises flavors or a flavoring agent. In some embodiments, the flavor or flavoring agent is peppermint. In some embodiments, the flavor or flavoring agent is present in an amount of about 0.1 to about 5%, by weight, of the composition. In a particular example, the flavoring agent is present in an amount of about 1%, by weight.

In a certain embodiment, the mucoadhesive composition comprises:

| | |
|---|---|
| Triamcinolone | about 0.01%-about 5% |
| Phenol | about 0.5%-about 10% |
| Mucoadhesive polymer | about 0.1%-about 10% | wherein the mucoadhesive polymer is selected from the group consisting of CARBOPOL® 974 P NF, CARBOPOL® ETD 2020 NF, CARBOPOL® 971 P, and CARBOPOL® 934 P

| | |
|---|---|
| Flavoring | about 0.5%-about 10% |
| Water (with a preservative) | QS to desired volume. |

In a particular embodiment, the mucoadhesive composition comprises:

| | |
|---|---|
| Triamcinolone | about 0.044% |
| Phenol | about 1.5% |
| CARBOPOL ® 974 P NF | about 1.0% |
| Peppermint flavor | about 1.0% |
| Water (preserved with parabens) | QS to desired volume |

In a particular embodiment, the mucoadhesive composition comprises:

| | |
|---|---|
| Triamcinolone | about 0.044% |
| Phenol | about 1.5% |
| CARBOPOL ® ETD 2020 NF | about 1.0% |
| Peppermint flavor | about 1.0% |
| Water (preserved with parabens) | QS to desired volume |

In a particular embodiment, the mucoadhesive composition comprises:

| | |
|---|---|
| Triamcinolone | about 0.044% |
| Phenol | about 1.5% |
| CARBOPOL ® 971P | about 0.25% |
| Peppermint flavor | about 1.0% |
| Water (preserved with parabens) | QS to desired volume |

In a particular embodiment, the mucoadhesive composition comprises:

| | |
|---|---|
| Triamcinolone | about 0.044% |
| Phenol | about 1.5% |
| CARBOPOL ® 934P | about 1.0% |
| Peppermint flavor | about 1.0% |
| Water (preserved with parabens) | QS to desired volume |

C. Spray Devices

The present disclosure also provides a spray device comprising a therapeutically effective amount of a mucoadhesive composition described herein. In an embodiment, the spray device is adapted for oral delivery of a pharmaceutical composition to a patient. A skilled artisan can design the spray device to deliver a desired amount of a formulation in accordance with patients' needs (e.g., a therapeutically effective amount). In an embodiment, a spray volume is between about 0.1 and about 1.0 mL. In a particular embodiment, the spray device delivers a spray volume of about 0.5 mL. In an embodiment, each pump delivers a therapeutically effective amount of the active agent. In an embodiment, the pump has manual actuation. In an embodiment, the pump has an extended nozzle. In a particular example, the pump is a chloraseptic-type pump.

D. Methods for Delivering an Active Agent

The present disclosure also provides for a method for delivering an active agent to the mucosa, wherein the active agent is a component of a mucoadhesive composition comprising the active agent, a mucoadhesive polymer, and water.

In one embodiment is provided a method for delivering one or more active agents to the oral cavity comprising administering a mucoadhesive composition described herein to the oral cavity of a subject. The mucoadhesive polymer may be selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly (acrylic acid), poloxamer, galactomannan, glucomannan, carrageenan, hyaluronic acid, gelatin, lectin, fimbrial proteins, and combinations thereof. The active agent is selected from the group consisting of steroids, anti-viral agents, antibiotics, anesthetics, analgesics, hormones, opioids, and combinations thereof. In a further embodiment, the active agent is selected from the group consisting of triamcinolone, acyclovir, famcyclovir, valacyclovir, benzocaine, phenol, penicillin, amoxicillin, insulin, and combinations thereof.

In another embodiment, the mucoadhesive composition is applied to the oral cavity, including, but not limited to, the posterior oropharynx, the anterior oropharynx, or under the tongue (sublingually).

In an embodiment, the method makes a residence time of the active agent not less than about 5 minutes. In an embodiment, the method makes a residence time of the active agent not less than about 10 minutes. In another embodiment, the residence time of the active agent is not less than about 20 minutes. In yet another embodiment, the residence time of the active agent is not less than about 30 minutes. As used herein, "residence time" is the length of time the spray stays on the posterior pharynx.

E. Methods of Treatment

The present disclosure also provides for a method for treating a disease, disorder, or condition comprising administering a mucoadhesive composition described herein to a mucosal membrane of a subject. In an embodiment, the administration of a mucoadhesive composition is carried out with a spray device. The mucoadhesive polymer may be selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer, galactomannan, glucomannan, carrageenan, hyaluronic acid, gelatin, lectin, fimbrial proteins, and combinations thereof, wherein said disease, disorder, or condition is amenable to treatment from said mucoadhesive composition.

In another embodiment, the subject receiving the mucoadhesive composition suffers from a disease, disorder, or condition selected from the group consisting of pharyngitis, aphthous stomatitis (canker sore), bacterial infection, radiation-induced mucositis, fibromyalgia, chronic fatigue syndrome (CFS), myalgic encephalomyelitis/chronic fatigue syndrome (ME/CFS), and diabetes.

The term "pharyngitis" includes viral and bacterial pharyngitis. Causes of viral pharyngitis include, but are not limited to, rhinovirus, adenovirus, Epstein-Barr virus (EBV), herpes simplex virus (HSV) type 1, HSV type 2, influenza virus, parainfluenza virus, coronavirus, enterovirus, respiratory syncytial virus (RSV), cytomegalovirus (CMV), and human immunodeficiency virus (HIV). The cause of bacterial pharyngitis includes, but is not limited to, beta-hemolytic streptococci, including group A beta-hemolytic streptococci (GABHS).

The term "radiation-induced mucositis" refers to the mucositis, such as oral mucositis, caused or induced by radiation, such as radiation for cancer therapy. The disease includes oral erythematous and ulcerative lesions and may be initiated by direct injury to the basal epithelial cells or cells in the underlying tissue. The damage may be from DNA-strand breaks or non-DNA injury. The radiation-induced mucositis may also be mediated by activation of pro-inflammatory activators, such as macrophages releasing pro-inflammatory cytokines (e.g., TNF-α and IL-6).

The term "fibromyalgia" encompasses both fibromyalgia and fibromyalgia syndrome. Fibromyalgia is a medical disorder characterized by chronic widespread pain and other symptoms, including but not limited to fatigue, insomnia, depression, allodynia, headaches, irritable bowel syndrome, sensitivity to light, numbness and anxiety symptoms.

"Irritable bowel syndrome" (IBS) is a common disorder that affects the large intestine. Patients with IBS suffer abdominal pain at least three times a month, not caused by generalized anxiety disorder (GAD), other disease or injury.

The terms "chronic fatigue syndrome" and "myalgic encephalomyelitis/chronic fatigue syndrome" may be referred to as systemic exertion intolerance disease (SEID). CFS and ME/CFS may be caused by viruses (including, but not limited to, Epstein-Barr virus, human herpes virus 6, enterovirus, rubella, bornavirus, Ross River virus, and retroviruses), allergies, hypotension, a weakened immune system, and/or hormonal imbalances. Symptoms of CFS and ME/CFS include, but are not limited to, feeling unwell for more than 24 hours after physical activity, muscle pain, memory problems, headaches, pain in multiple joints, sleep problems, sore throat, and tender lymph nodes.

The term "diabetes" encompasses all types of diabetes, and complications therefrom, including, but not limited to, type 1 diabetes mellitus; type 2 diabetes mellitus; gestational diabetes; prediabetes; latent autoimmune diabetes of adults (LADA); congenital diabetes; cystic fibrosis-related diabetes; diabetes caused by insulin-antagonistic hormones; diabetes due to genetic defects of insulin secretion; diabetes due to high doses of glucocorticoids, steroids, β-adrenergic agonists, statins, or thyroid hormones; diabetes due to chronic pancreatitis, pancreatectomy, hemochromatosis, fibrocalculous pancreatopathy, acromegaly, Cushing syndrome, hyperthyroidism, pheochromocytoma, or glucagonoma; and diabetes due to infection (e.g., infection by cytomegalovirus or coxsackievirus B). Complications of diabetes include, but are not limited to, diabetic retinopathy, diabetic nephropathy, diabetic neuropathy, and diabetes-related foot problems (e.g., diabetic foot ulcers).

Bacterial infections include, but are not limited to, gram-positive bacteria. In some embodiments, the bacteria causing the infection includes, but is not limited to, the genus *Bacillus, Enterococcus, Listeria, Neisseria, Staphylococcus, Candida*, and *Streptococcus*.

In a particular embodiment, the subject receiving the mucoadhesive composition suffers from viral pharyngitis. In a further embodiment, the mucoadhesive composition comprises triamcinolone, acyclovir, and either benzocaine or phenol, and the subject receiving said composition suffers from viral pharyngitis.

In another embodiment, the subject receiving the mucoadhesive composition suffers from aphthous stomatitis (canker sore). In a further embodiment, the mucoadhesive composition comprises triamcinolone, and either benzocaine or phenol, and the subject receiving said composition suffers from aphthous stomatitis (canker sore).

In another embodiment, the subject receiving the mucoadhesive composition suffers from fibromyalgia. In a further embodiment, the mucoadhesive composition comprises acyclovir, famcyclovir, or valacyclovir, and the subject receiving said composition suffers from fibromyalgia.

In another embodiment, the subject receiving the mucoadhesive composition suffers from diabetes. In a further embodiment, the mucoadhesive composition comprises insulin, and the subject receiving said composition suffers from diabetes.

In another embodiment, the subject receiving the mucoadhesive composition suffers from radiation-induced mucositis. In a further embodiment, the subject receiving the mucoadhesive composition comprises triamcinolone and dextro-naltrexone, and the subject suffers from radiation-induced mucositis.

In another embodiment, the subject receiving the mucoadhesive composition suffers from bacterial infection. In a further embodiment, the mucoadhesive composition comprises penicillin, and the subject receiving said composition suffers from bacterial infection.

The mucoadhesive compositions of the present disclosure can be administered in a unit dosage form. If desired, multiple doses per day of the unit dosage form can be used to increase the total daily dose.

In another embodiment, the daily dose of triamcinolone is between about 0.01 and about 25 mg. In a particular embodiment, the daily dose of triamcinolone is about 220 μg. Alternatively, the daily dose of triamcinolone may be between about 0.01 and about 0.5%, by weight, of the spray. In a particular alternative embodiment, the daily dose of the triamcinolone may be present in about 0.044%, by weight, of the spray.

In another embodiment, the daily dose of benzocaine is between about 1 and about 100 mg. In a particular embodiment, the daily dose of benzocaine is about 10 mg.

In another embodiment, the daily dose of phenol is between about 0.5% and about 3% of the spray volume. In a particular embodiment, the daily dose of phenol is about 1.4% of the spray volume.

In another embodiment, the daily dose of acyclovir, famcyclovir, and valacyclovir is between about 0.01 and about 10 mg/cm$^2$. In a particular embodiment, the dose of acyclovir is between about 10 and about 200 mg. In a particular embodiment, the dose of famciclovir or valacyclovir is between about 10 and about 250 mg.

In another embodiment, the daily dose of insulin is between about 1 and about 200 IU. In a particular embodiment, the daily dose of insulin is between about 10 and about 150 IU.

In another embodiment, the mucoadhesive composition of the present disclosure can be administered via a spray device.

In another embodiment, the spray device delivers the mucoadhesive composition in a spray volume between about 0.1 and about 1.0 mL. In a particular embodiment, the spray volume of is about 0.5 mL.

In another embodiment, the spray device includes an operating mechanism (e.g., a spray head or a pump) attached to a fluid reservoir. In another embodiment, the spray device may be manually actuated or pressurized.

EXAMPLE

Example 1: Determination of Spray Properties of Mucoadhesive Compositions

The present disclosure can be understood as a method for delivering a mucoadhesive composition comprising an active agent, a mucoadhesive polymer, and water, to the oral cavity, for example the posterior oropharynx, wherein said mucoadhesive composition adheres to the mucosa, thereby delivering the active agent for local or systemic effects.

When formulating the mucoadhesive composition of the present claims, the inventors assayed numerous aqueous polymer compositions to determine desirable and/or effective adhesion and spray area properties. The polymer compositions included sodium alginate (2 and 4 wt %), chitosan (3 wt % in 1% lactic acid), guar gum (1.5 wt %), xanthan gum (1.7 wt %), pectin (3 wt %), 2-hydroxyl cellulose (90 k or 250 k g/mol; 5 wt %), hydroxypropyl cellulose (80 k or 100 k g/mol; 0.1M), hydroxypropylmethyl cellulose (80-120, 2600-5600 cP; 2% wt/vol), sodium carboxymethyl cellulose (90 k or 250 k g/mol; 4 wt %), poly(ethylene oxide) (100 k, 200 k, or 300 k g/mol), CARBOPOL® 971P NF, CARBOPOL® 974P NF, CARBOPOL® 934P NF, CARBOPOL® ETD 2020 FN, and poloxamer (pluronic F-127/ poloxamer 407; 25%)

Tanned leather was used as a mucus mimic (see Blanco-Fuente, et al., *Int. J. Pharma.* 1996) due to its having similar mucoadhesive properties compared to biological mucosa, and being simple to obtain. The mucoadhesive properties of various aqueous polymer solutions were determined by spraying them with a chloroseptic-type pump onto dry, leather mucus mimic pieces (3.5 inches×3.5 inches) from a distance of approximately 3.5 inches, which is approximately the distance between the opening of the mouth and the throat. The aqueous mucoadhesive polymer compositions were assayed for spray area and adhesion, as demonstrated by the amount of beading or dripping following spray application. Polymer concentrations were considered too low if the spray area was small and too high if low adhesion (shown by excessive dripping) was observed. Table 1 shows the results of the tests to determine the mucoadhesive polymer concentration for effective and/or desirable spray area and adhesion of the various aqueous polymer compositions. Photographs of the compositions comprising CARBOPOL® 974P NF, CARBOPOL® 971P, CARBOPOL® ETD 2020 NF, CARBOPOL® 934P, pectin, and chitosan are shown in FIG. 1.

TABLE 1

| Polymer | 15% | 10% | 6% | 4% | 3% | 2% | 1% | 0.5% | 0.25% | 0.15% |
|---|---|---|---|---|---|---|---|---|---|---|
| CARBOPOL ® 974P* | - | - | - | - | - | - | T | + | T | - |
| CARBOPOL ® 971P* | - | - | - | - | - | - | T | T | + | T |
| CARBOPOL ® ETD 2020 NF* | - | - | - | - | - | T | + | T | - | - |
| CARBOPOL ® 934P* | - | - | - | - | - | T | + | T | - | - |
| Pectin* | - | - | - | - | T | T | + | T | - | - |
| Chitosan* | - | - | - | - | - | - | T | + | - | - |
| NaCMC (90k g/mol) | - | - | - | T | - | + | T | - | - | - |
| NaCMC (250k g/mol) | - | - | - | - | - | T | + | T | - | - |
| HEC (90k g/mol) | - | - | T | T | - | + | - | - | - | - |
| HEC (250k g/mol) | - | - | - | - | - | T | + | - | - | - |
| HPMC (80-120 cP) | - | - | - | - | - | T | T | + | - | - |
| HPMC (2600-5600 cP) | - | - | - | - | - | - | T | T | + | - |
| HPC (80k g/mol) | - | - | - | T | - | + | T | - | - | - |
| HPC (100k g/mol) | - | - | - | T | - | + | T | - | - | - |
| PEO (300k g/mol) | - | - | - | - | T | - | T | T | - | - |
| Pluronic F-127 | T | + | - | - | - | - | - | - | - | - |
| Sodium alginate | - | - | - | - | - | T | + | T | - | - |
| Xanthan gum | - | - | - | - | - | - | T | T | T | - |

Figure 2:
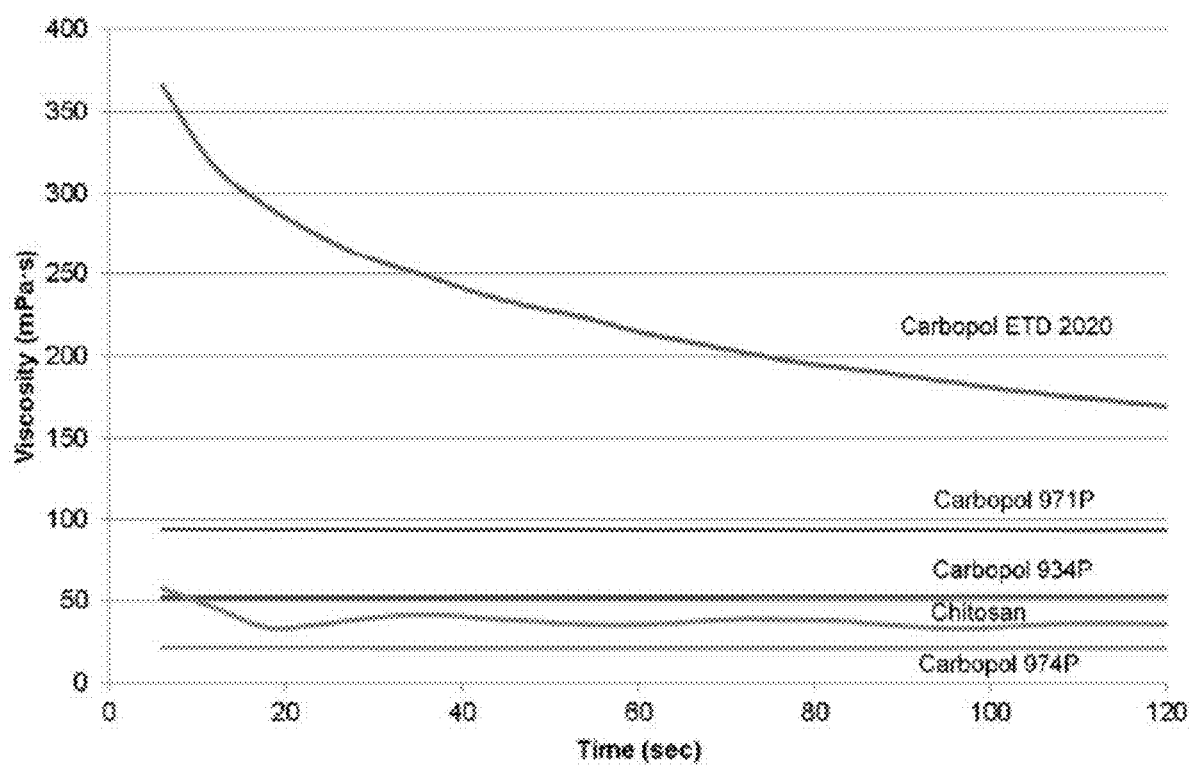
FIG. 2 measures the viscosity of mucoadhesive composition.
Figure 3A:
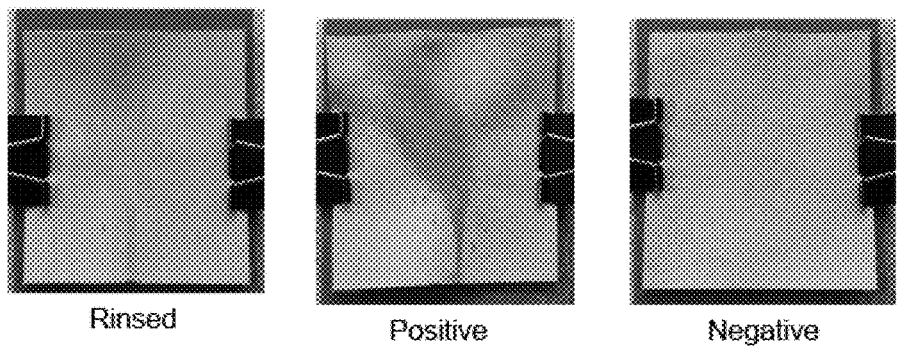
FIGS. 3A, 3B, 3C, 3D, and 3E show the adhesiveness of mucoadhesive composition before and after a rinse with artificial saliva. 3A: 1% CARBOPOL® EDT 2020 NF; 3B: 1% CARBOPOL® 934P; 3C: 0.5% CARBOPOL® 974P; 3D: 0.25% CARBOPOL® 971P; and 3E: 0.5% Chitosan.
Figure 3B:
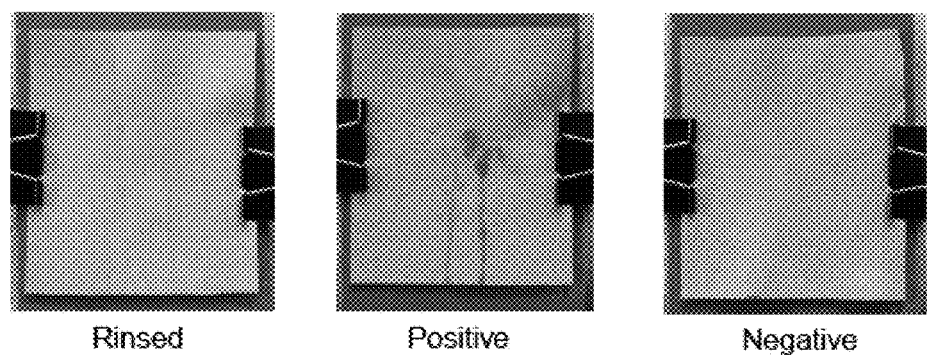
Figure 3C:
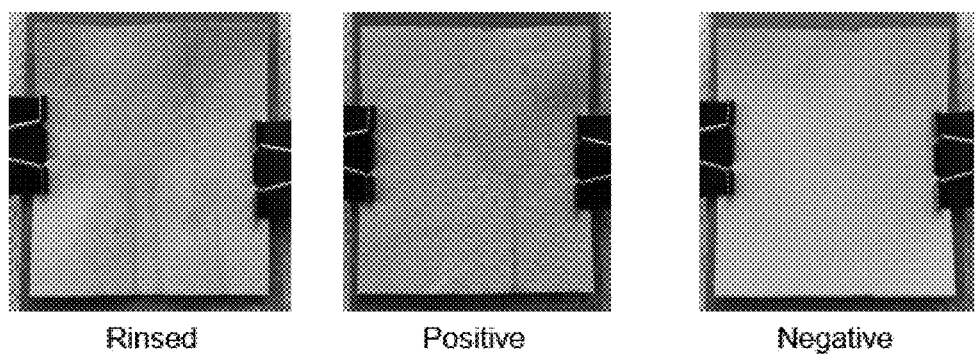
Figure 3D:
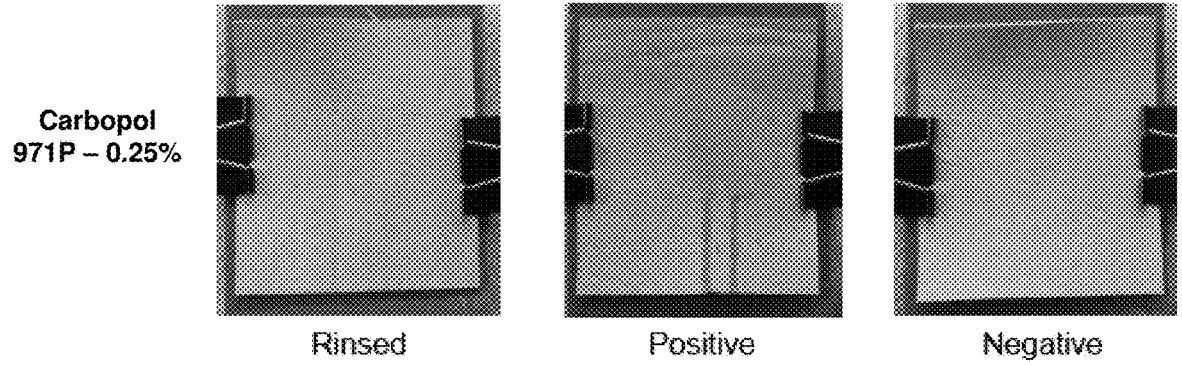
Figure 3E:
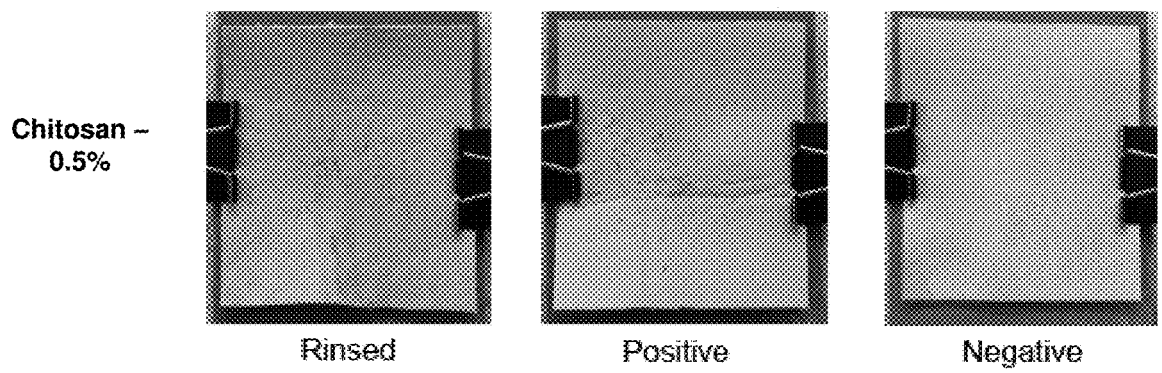

Legend:
* = shown in FIG. 1
+ = concentration for desirable spray area and adhesion
T = tested for spray area and/or adhesion
− = not tested Polymer viscosity was characterized with a rheometer which applied a shear rate of 50 s$^{-1}$ for 2 minutes at room temperature and measured the resulting viscosity (FIG. 2). CARBOPOL® ETD 2020 NF displayed shear thinning, which is desirable since it provides for a higher concentration of the active agent while maintaining a large spray area. The increased concentration of the active agent led to increased adhesion and allows for more of the active agent to be administered.

Drug residence time in the oral cavity can be a challenge for pharmaceutical compositions applied to oral mucosal surfaces. Drug residence time is typically short (<5 to 10 minutes) due to continuous secretion and flow of saliva (0.5 to 2 L/day) and mobility of tissues. Mucoadhesive formulations can overcome this problem by accompanying the active agent with one or more mucoadhesive polymers to provide high local concentrations of the active agent to a relatively small region within the mouth. The mucoadhesive polymers, in essence, carry the active agent to the target location.

To address this challenge, the inventors assayed the mucoadhesive aqueous polymer compositions for their ability to resist being washed away by saliva. Artificial saliva was prepared according to Preetha, et al. (*Trends Biomater. Artif. Organs* 2005), to include:

5 mM sodium bicarbonate;
7.36 mM sodium chloride;
20 mM potassium chloride;
6.6 mM sodium dihydrogen phosphate monohydrate;
1.5 mM calcium chloride dehydrate; and,
10 g/L sodium carboxymethyl cellulose (90 kg/mol).

These salts were mixed with deionized water.

The polymer solutions of FIG. 1 were mixed with PROsperse disperse dye and sprayed onto leather mucus mimic, as described above. The leather pieces were then rinsed with 5 mL artificial saliva by dripping the artificial saliva across the sprayed surface with a syringe. All sprayed leather samples similarly retained a red color (due to the PROsperse disperse dye) after rinsing with artificial saliva and were more similar in appearance to the unrinsed ("positive" samples) than to the leather mucus mimic washed with DI water to remove the spray (FIG. 3). The red color retention is not due to staining of the leather mucus mimic since the negative control (complete removal of sprayed formulation) is free of the dye. These results demonstrate that each polymer solution remained on the leather mucus mimic after rinsing with artificial saliva.

Figure 4:
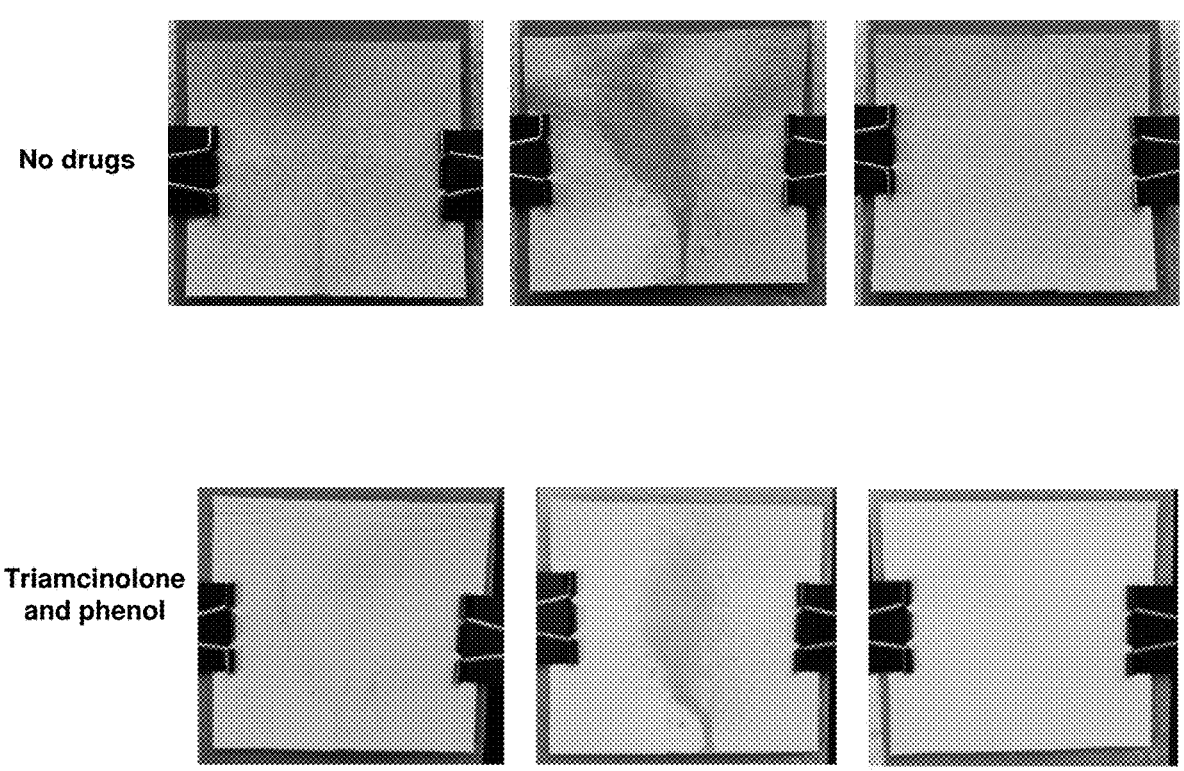
FIG. 4 shows the adhesiveness of mucoadhesive composition containing triamcinolone and phenol.

Based on these results, 6 polymers (CARBOPOL® 974P, CARBOPOL® 971P, CARBOPOL® 934P, CARBOPOL® ETD 2020 NF, pectin, and chitosan) were identified for further study. Triamcinolone (220 µg/0.5 mL spray; 0.044%) and phenol (1.4%) were added to a 1% solution of CARBOPOL® ETD 2020 NF to test the effect of a drug combination on solution's mucoadhesive properties. The presence of triamcinolone and phenol did not significantly affect the mucoadhesive properties of the CARBOPOL® ETD 2020 NF solution, as the drug-containing solution exhibited good adhesion, minimal dripping, and desirable spray area (FIG. 4). Further, the addition of an active agent (triamcinolone and phenol) did not negatively affect the capacity of the mucoadhesive formulation to adhere to the leather mucus mimic, as a rinse with the artificial saliva did not remove the polymer spray which contained the active agents. This study demonstrates that the CARBOPOL® sprays possessed desirable properties for the mucoadhesive polymer to durably deliver an active agent to a mucosal membrane with an acceptable retention time.

Figure 5:
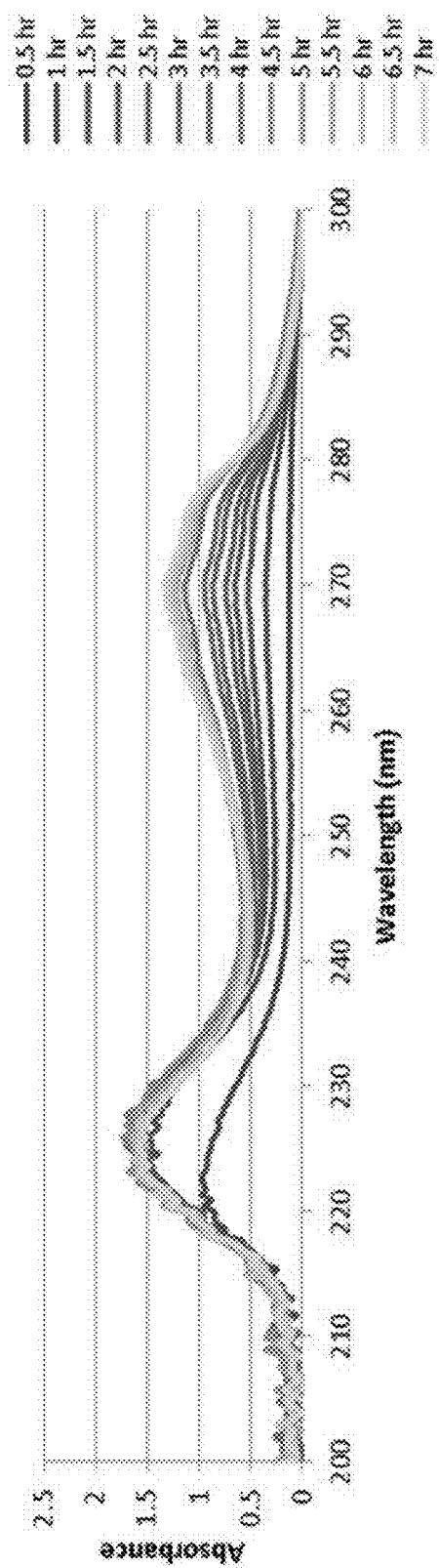
FIG. 5 measures the release of triamcinolone and phenol from a mucoadhesive composition comprising the drugs, CARBOPOL® ETD 2020 NF, and water. The mucoadhesive composition was applied to lamb mucosa and drug release was evaluated via a flow-through Franz diffusion cell.

The mucoadhesive composition of the present disclosure not only delivers an active agent to a surface of the oral cavity, the active agent is capable of diffusing across buccal mucosa (FIG. 5). Drug release through lamb buccal mucosa was evaluated via a flow-through Franz diffusion cell. Lamb buccal mucosa was clamped into the cell and the receptor chamber was filled with 5 mL of phosphate buffered solution (PBS). CARBOPOL® ETD 2020 NF (1%) solution containing triamcinolone and phenol was applied to the donor chamber. 0.5 mL of PBS was withdrawn from the receptor chamber every 30 minutes and replaced with fresh PBS over the course of 7 hours. Each sample was placed in a cuvette for testing via UV-Vis spectrophotometry. The sample was compared to a set of calibration standards of known concentrations for triamcinolone and phenol, independently. Increasing amounts of triamcinolone and phenol were released over time from the mucoadhesive composition and diffused through the lamb buccal mucosa. The peaks at 225 nm and 270 nm correspond to phenol, and the peak at 240 corresponds with triamcinolone. Phenol diffusion through the mucosa was less than 0.025% based on calibration curve. The triamcinolone peak was difficult to quantify because it overlapped with the phenol peaks.

The disclosed series of spray formulations prepared and tested by the above methods are representative of the present disclosure. The addition of an active agent does not negatively affect the mucoadhesive properties of the formulations. The representative mucoadhesive spray formulations retain their adhesiveness upon rinsing with artificial saliva and are capable of delivering an active agent through buccal mucosa.

Example 2: Treatment of Viral Pharyngitis

NRP-1, a composition comprising 0.044% triamcinolone (220 µg/0.54 mL), 1.5% phenol, 1% CARBOPOL® 974P NF, and 1% flavoring (peppermint) dissolved in water with parabens as a preservative, was provided to each of 15 individuals suffering from acute, recurring pharyngitis. Six ounces of the solution was provided in an appropriate spray bottle with a long nozzle. The subjects sprayed the posterior oropharynx with one to three sprays, each spray being a volume between about 0.17 and about 0.29 mL of the above solution. The solution was administered every 8 hours, as needed Pain scores (1-10) were provided by subjects before and immediately following application, and at 1, 5, 10, 20, and 60 minutes. The subjects also evaluated the taste (1-5) (i.e., bitterness) and perceived adequacy of coverage ("Area"). The results of the pre-clinical test are shown in Table 2 below.

TABLE 2

| | Initial | | | Pain following administration (minutes) | | | | | | |
|---|---|---|---|---|---|---|---|---|---|---|
| Patient | Pain | Days in Pain | Area | 0 | 1 | 5 | 10 | 20 | 60 | Taste |
| 1 | 8 | 12 | 6 | 1 | 0.5 | 0 | 0 | 0 | 0 | 3 |
| 2 | 4 | 10 | 8 | 1 | 1 | 1 | 2 | 2 | 2 | 3 |
| 5 | 7 | 10 | 10 | 5 | 0.5 | 0 | 0 | 0.5 | 0.5 | 4 |
| 6 | 9 | 5 | 8 | 1 | 1 | 0 | 0 | 1 | 3 | 3 |
| 9 | 8 | 1 | 8 | 5 | 4 | 3 | 3 | 2 | 1 | 3 |
| 11 | 7 | 5 | 10 | 0 | 0 | 0 | 0 | 0 | 0 | 3 |
| 13 | 5 | 7 | 10 | 0 | 0 | 0 | 0 | 0 | 2 | 3 |
| 15 | 7 | 8 | 10 | 1 | 0 | 0 | 0 | 0 | 1 | 3 |
| 19 | 10 | 3 | 10 | 2 | 2 | 2 | 1 | 1 | 0 | 3 |
| 22 | 6 | 10 | 8 | 5 | 5 | 4 | 4 | 3 | 3 | 3 |

TABLE 2-continued

| Patient | Initial Pain | Days in Pain | Area | Pain following administration (minutes) | | | | | | Taste |
|---|---|---|---|---|---|---|---|---|---|---|
| | | | | 0 | 1 | 5 | 10 | 20 | 60 | |
| 28 | 5 | 10 | 8 | 7 | 6 | 4 | 0 | 0 | 0 | 2 |
| 31 | 8 | 5 | 10 | 6 | 6 | 5 | 5 | 4 | 4 | 3 |
| 33 | 5 | 2 | 8 | 2 | 1 | 0 | 0 | 0 | 0 | 3 |
| 32 | 9 | 6 | 9 | 4 | 3 | 2 | 1 | 2 | 1 | 3 |
| 35 | 6 | 4 | 8 | 2 | 1 | 1 | 1 | 1 | 1 | 2 |
| Sum | 104 | 98 | 131 | 42 | 31 | 22 | 17 | 16.5 | 18.5 | 44 |
| Avg | 6.9 | 6.5 | 8.7 | 2.8* | 2.1* | 1.5* | 1.1* | 1.1* | 1.2* | 2.9 |
| StDev | 1.8 | 3.4 | 1.2 | 2.3 | 2.2 | 1.8 | 1.6 | 1.3 | 1.3 | 0.5 |

*p < 0.05 per paired Student's T test compared to initial pain score.

As shown above, the study subjects presented with an initial average acute pharyngitis-induced throat pain score of 6.9±1.8, with 11 of 15 (73.3%) having been in pain for 5 or more days prior to the trial. Immediately following administration of NRP-1, there was a statistically significant reduction in reported throat pain scores which was maintained over the course of an hour. The NRP-1 spray had an acceptable coverage area, with an average reported coverage score of 8.7±1.2 and 14 of 15 subjects (93.3%) reporting a coverage score of 8 or greater. Further, NRP-1 had an acceptable taste, with an average taste score of 2.9±0.5. These results demonstrate that NRP-1 is effective in ameliorating throat pain due to acute recurring pharyngitis.

Example 3: Treatment of Radiation-Induced Mucositis

In this method, subjects suffering from radiation-induced mucositis and in need of treatment are identified via observation from a health care provider. Compositions comprising a mucoadhesive polymer, triamcinolone, phenol, and water are administered via a spray device to the posterior oropharynx at a dose suitable to treat the radiation-induced mucositis. The mucoadhesive polymer will allow the triamcinolone and phenol to adhere to the posterior oropharynx for a time sufficient to treat the radiation-induced mucositis.

Example 4: Treatment of Aphthous Stomatitis

In this method, subjects suffering from aphthous stomatitis (canker sore) and in need of treatment are identified via observation from a health care provider. Compositions comprising the mucoadhesive polymer, triamcinolone, and water are administered via a spray device to the posterior oropharynx, at a dose suitable to treat the aphthous stomatitis (canker sore). The mucoadhesive polymer will allow the active agents to adhere to the posterior oropharynx for a time sufficient to treat the aphthous stomatitis.

Example 5: Treatment of Fibromyalgia

In this method, subjects suffering from fibromyalgia and in need of treatment are identified via observation from a health care provider. Compositions comprising the mucoadhesive polymer, famcyclovir or valacyclovir, and water are administered via a spray device to the posterior oropharynx, at a dose suitable to treat the fibromyalgia. The mucoadhesive polymer will allow the active agents to adhere to the posterior oropharynx for a time sufficient to treat the fibromyalgia.

Example 6: Treatment of Diabetes

In this method, subjects suffering from diabetes and in need of treatment are identified via observation from a health care provider and/or tests indicating elevated blood glucose levels. Compositions comprising the mucoadhesive polymer, insulin, and water are administered via a spray device to the posterior oropharynx, at a dose suitable to treat the diabetes. The mucoadhesive polymer will allow the active agents to adhere to the posterior oropharynx for a time sufficient to treat the diabetes.

All mentioned documents are incorporated by reference as if herein written. When introducing elements of the present disclosure or the exemplary embodiment(s) thereof, the articles "a," "an," "the," and "said" are intended to mean that there are one or more of the elements. The terms "comprising," "including," and "having" are intended to be inclusive and mean that there may be additional elements other than the listed elements. Although this invention has been described with respect to specific embodiments, the details of these embodiments are not to be construed as limitations.

What is claimed is:

1. A method for delivering an active agent to the oral cavity comprising:
    administering to the oral cavity of a subject in need thereof a mucoadhesive composition comprising
        about 0.01-0.5%, by weight, triamcinolone;
        about 0.5-3%, by weight, phenol;
        about 0.1-5.0%, by weight, peppermint flavor; and
        a mucoadhesive polymer, wherein the mucoadhesive polymer is selected from the group selected from the group consisting of about 0.25-1.0%, by weight, carbopol 974 P NF; about 0.5-2.0%, by weight carbopol ETD 2020 NF; about 0.25-1.0%, by weight, carbopol 971P; and about 0.5-2.0%, by weight, carbopol 934P, and
    wherein a viscosity of the mucoadhesive polymer is between 50 and 600 mPa·s.

2. The method of claim 1, wherein the composition is administered via spray.

3. The method of claim 1, wherein the composition is applied to the posterior oropharynx.

4. The method of claim 1, wherein the subject suffers from a disease, disorder, or condition selected from the group consisting of pharyngitis, aphthous stomatitis, bacterial infection, radiation-induced mucositis, fibromyalgia, and diabetes.

5. A method for palliative treatment of a disease, disorder, or condition comprising:
    administering a mucoadhesive composition to the oral cavity of a subject in need of such treatment;
    wherein the mucoadhesive composition comprises
        about 0.01-0.5%, by weight, triamcinolone;
        about 0.5-3%, by weight, phenol;
        about 0.1-5.0%, by weight, peppermint flavor; and a mucoadhesive polymer, wherein the mucoadhesive polymer is selected from the group selected from the group consisting of about 0.25-1.0%, by weight, carbopol 974 P NF; about 0.5-2.0%, by weight carbopol ETD 2020 NF; about 0.25-1.0%, by weight, carbopol 971P; and about 0.5-2.0%, by weight, carbopol 934P, wherein a viscosity of the mucoadhesive polymer is between 50 and 600 mPa·s, and wherein the composition is administered via spray, and wherein the disease, disorder, or condition is selected from the group consisting of pharyngitis, aphthous stomatitis, bacterial infection, radiation-induced mucositis, fibromyalgia, chronic fatigue syndrome, myalgic encephalomyelitis/chronic fatigue syndrome, and diabetes.

6. The method of claim 5, wherein the disease is selected from the group consisting of viral pharyngitis, radiation-induced mucositis, aphthous stomatitis, fibromyalgia, and diabetes.

7. The method of claim 6, wherein the disease is viral pharyngitis.

8. The method of claim 5, wherein the mucoadhesive composition is applied to the posterior oropharynx, anterior oropharynx, or sublingually.

9. A mucoadhesive composition comprises
about 0.01-0.5%, by weight, triamcinolone;
about 0.5-3%, by weight, phenol;
about 0.1-5.0%, by weight, peppermint flavor; and
a mucoadhesive polymer, wherein the mucoadhesive polymer is selected from the group selected from the group consisting of about 0.25-1.0%, by weight, carbopol 974 P NF; about 0.5-2.0%, by weight carbopol ETD 2020 NF; about 0.25-1.0%, by weight, carbopol 971P; and about 0.5-2.0%, by weight, carbopol 934P, and wherein a viscosity of the mucoadhesive polymer is between about 50 and about 600 mPa·s.

10. The mucoadhesive composition of claim 9, wherein the composition is formulated for administration via spray.

11. The mucoadhesive composition of claim 9, comprising
about 0.044%, by weight, triamcinolone;
about 1.5%, by weight, phenol;
about 1.0%, by weight, Carbopol 974 P NF; and
about 1.0%, by weight, peppermint flavor.

12. The mucoadhesive composition of claim 9, comprising
about 0.044%, by weight, triamcinolone;
about 1.5%, by weight, phenol;
about 1.0%, by weight, Carbopol ETD 2020 NF; and
about 1.0%, by weight, peppermint flavor.

13. The mucoadhesive composition of claim 9, comprising
about 0.044%, by weight, triamcinolone;
about 1.5%, by weight, phenol;
about 0.25%, by weight, Carbopol 971P; and
about 1.0%, by weight, peppermint flavor.

14. The mucoadhesive composition of claim 9, comprising
about 0.044%, by weight, triamcinolone;
about 1.5%, by weight, phenol;
about 1.0%, by weight, Carbopol 934P; and
about 1.0%, by weight, peppermint flavor.

* * * * *